(12) United States Patent
Franzreb et al.

(10) Patent No.: US 8,158,007 B2
(45) Date of Patent: Apr. 17, 2012

(54) METHOD FOR MAGNETICALLY SUPPORTED EXTRACTION

(75) Inventors: Matthias Franzreb, Karlsruhe (DE); Joerg Becker, Darmstadt (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 358 days.

(21) Appl. No.: 12/597,952

(22) PCT Filed: Apr. 23, 2008

(86) PCT No.: PCT/EP2008/003245
§ 371 (c)(1),
(2), (4) Date: Oct. 28, 2009

(87) PCT Pub. No.: WO2008/131891
PCT Pub. Date: Nov. 6, 2008

(65) Prior Publication Data
US 2010/0116747 A1   May 13, 2010

(30) Foreign Application Priority Data
Apr. 28, 2007   (DE) .......................... 10 2007 020 220

(51) Int. Cl.
*B01D 29/00* (2006.01)
(52) U.S. Cl. ..................................... 210/695
(58) Field of Classification Search .................... 210/695
See application file for complete search history.

(56) References Cited

U.S. PATENT DOCUMENTS
6,521,341 B1   2/2003   Elaissari et al.

FOREIGN PATENT DOCUMENTS
DE          69925241 T2     1/2006
DE          102005034327 B3   11/2006
WO          WO 03089906 A2   10/2003

OTHER PUBLICATIONS

Albertsson, P.A.: Partition of Cell Particles and Macromolecules, New York: Wiley (1986).
Flygare, S. et al.: Magnetic aqueous two-phase separation in preparative applications, Enzyme Microb. Tech., 12 (1990) 95-103.
Johansson, G.: Aqueous two-phase systems in protein purification, J. Biotech. 3 (1985) 11-18.
Scopes. R. K.; Protein purification in the nineties. Biotechnol. Appl. Biochem., 23 (1996) 197-204.
Suzuki, M. et al.: Affinity Partitioning of Protein A using a Magnetic Aqueous Two-Phase System, J. Ferment. Bioeng. 80 (1995) 78-84.

(Continued)

*Primary Examiner* — Chester Barry
(74) *Attorney, Agent, or Firm* — Leydig, Voit & Mayer, Ltd.

(57) ABSTRACT

A method for magnetically assisted extraction of a target substance from an aqueous solution containing a plurality components includes mixing a surfactant and functional magnetic particles having affinity for the target substance into the aqueous solution containing the target substance so as to bind the target substance to the functional magnetic particles and form a particle-containing single-phase aqueous surfactant solution. The particle-containing single-phase aqueous surfactant solution is transitioned to a two-phase state, a first particle- and surfactant-containing disperse phase being formed within a surrounding second phase. The first particle- and surfactant-containing disperse phase and the surrounding second phase are separated using a magnetic field. The first particle- and surfactant-containing disperse phase are separated.

14 Claims, 1 Drawing Sheet

OTHER PUBLICATIONS

Ullmanns Encyclopedia of Technical Chemistry, vol. B3, Chapter 11; Biochemical Separations.

Ullmanns Encyclopedia of Technical Chemistry, vol. B3, Chapter 6: Liquid-Liquid Extraction.

Wikstrom, P. et al.: Magnetically enhanced aqueous two-phase separation. In: Separation using aqueous phase systems, D. Fisher and LA. Sutherland, Editors. (1989) Plenum Publishing Corp. 455-461.

Wikstrom, P. et al: Magnetic aqueous two-phase separation: A new technique to increase rate of phase-separation, using dextran-ferrofluid or larger iron oxide particles. Anal. Biochem (1987) 167: 331-339.

Saitoh T. et al.: Use of Surfactant-Mediated Phase Separation (Cloud Point Extraction) with Affinity Ligands for the Extraction of Hydrophilic Proteins, Talanta, Elmsford, NY, US. vol. 42, No. 1, Jan. 1, 1995, pp. 119-127, XP000603770.

Franzreb M. et al.: Product Recovery by High-Gradient Magnetic Fishing, pp. 83-122, 2006.

METHOD FOR MAGNETICALLY SUPPORTED EXTRACTION

CROSS REFERENCE TO PRIOR APPLICATIONS

This application is a U.S. National Phase application under 35 U.S.C. §371 of International Application No. PCT/EP2008/003245, filed on Apr. 23, 2008, and which claims benefit to German Patent Application No. 10 2007 020 220.4, filed on Apr. 28, 2007. The International Application was published in German on Nov. 6, 2008 as WO 2008/131891 A1 under PCT Article 21(2).

FIELD

The present invention relates to a method for magnetically assisted extraction of a target substance from an aqueous solution containing several components.

BACKGROUND

An extraction method is a physical method for separating substances in which a component is extracted and separated from a mixture using an extraction agent. After separation, the extraction agent is removed. Extraction processes are important, in particular, in applications for processing biological or biochemical substances, namely for both obtaining and purifying such substances.

Examples of such processes are described in Ullmanns Encyclopedia of Technical Chemistry, Vol. B3, Chapter 6: Liquid-Liquid Extraction; Ullmanns Encyclopedia of Technical Chemistry, Vol. B3, Chapter 11: Biochemical Separations; Albertsson, P. A.: Partition of Cell Particles and Macromolecules, New York: Wiley (1986); Johansson, G.: Aqueous two-phase systems in protein purification, J. Biotech. 3 (1985) 11-18; and Scopes, R. K.: Protein purification in the nineties; Biotechnol. Appl. Biochem., 23 (1996) 197-204, which describe methods for extracting vitamins A and D from fish oils or the extraction of benzylpenicillin from a previously filtered fermentation broth. The sensitivity of complex biomolecules to non-polar solvents led to the development of what is known as ATPS methods (ATPS=Aqueous Two Phase Systems) (see Albertsson, P. A.: Partition of Cell Particles and Macromolecules, New York: Wiley (1986); Johansson, G.: Aqueous two-phase systems in protein purification, J. Biotech. 3 (1985) 11-18; and Scopes, R. K.: Protein purification in the nineties; Biotechnol. Appl. Biochem., 23 (1996) 197-204). ATPS are aqueous solutions of different hydrophilic polymers (such as polyethylene glycol (PEG), dextran), or of a polymer and inorganic salts (such as ammonium sulfate, potassium phosphate). Above critical concentrations of these components, the solution begins to separate into two phases, each of which is enriched in one of the components, and in which proteins are soluble without denaturation. See, for example, Ullmanns Encyclopedia of Technical Chemistry, Vol. B3, Chapter 11: Biochemical Separations. Now when a bio-suspension is converted into an ATPS, its components are each enriched in one of the two phases according to the respective distribution coefficients. Thus, for example in the case of a PEG-dextran system, the cell debris of a fermentation homogenate are predominantly found in the dextran phase, while the proteins go predominantly into the aqueous PEG phase.

A frequent problem of ATPS is insufficient distribution coefficients, which necessitate a multi-stage procedure that is time-consuming and requires complex apparatus. Therefore, in order to increase the selectivity of this separation method, the phase-forming polymers are selectively functionalized, for example, with affine ligands. As a result, the phase-forming polymers act specifically on a particular target molecule or a group of target molecules, selectively binding said molecules to themselves. Another fundamental problem is the very low surface tension at the phase interfaces which is due to the aqueous character of the two phases. Therefore, the system has only a weak tendency to reduce interfaces, and thus, for coalescence; i.e., the emulsions formed by mixing separate only very slowly. Frequently, centrifugation processes are used to remedy this problem. However, such processes require complex apparatus and, therefore, are cost-intensive and, in addition, have limited throughput. Moreover, if separation is performed on an industrial scale, large amounts of wastewaters with high polymer and salt contents are produced. Consequently, in addition to the resulting costs for chemicals, the cost of wastewater treatment also plays a role. Therefore, efforts are made to implement ATPS methods that allow recycling of at least one of the phases involved.

The references Wikström, P. et al.: Magnetic aqueous two-phase separation: A new technique to increase rate of phase-separation, using dextran-ferrofluid or larger iron oxide particles. Anal. Biochem. (1987) 167: 331-339; Wikström, P. et al.: Magnetically enhanced aqueous two-phase separation. In: Separation using aqueous phase systems, D. Fisher and I. A. Sutherland, Editors. (1989) Plenum Publishing Corp. 455-461; and Flygare, S. et al.: Magnetic aqueous two-phase separation in preparative applications, Enzyme Microb. Tech., 12 (1990) 95-103 describe an accelerated phase separation of ATPS, which is achieved by addition of magnetic particles. However, all of these approaches used non-functionalized magnetic nanoparticles or microparticles, so that the distribution coefficients of the system were not improved by the addition of said particles.

Therefore, Suzuki, M. et al.: Affinity Partitioning of Protein A using a Magnetic Aqueous Two-Phase System, J. Ferment. Bioeng. 80 (1995) 78-84 described using functional magnetic particles in combination with the ATPS method. In this connection, experiments were performed on a small batch scale (about 1 mL) to determine the distribution coefficient of immunoglobulins in the presence of added magnetic particles functionalized with protein A. In these experiments, a PEG-phosphate (ATPS) system was used, and the apparent distribution coefficient of the PEG-rich phase could be increased by a factor 4 to 35, depending on the experimental procedure, by adding the magnetic particles. However, this approach uses an ATPS of the aforementioned type without making any fundamental changes, so that there is still an enormous salt content to be expected in the resulting wastewater when implementing the method on an industrial scale. In addition, when a real cell homogenate is used, the resulting purity is not very high because the PEG-rich phase binds not only the desired substance, but also numerous other proteins.

This is why the use of a method known as "cloud point extraction" (CPE or CP-ATPS) is gaining importance in efforts to completely recycle the aforementioned ATPS. In the case of CP-ATPS, a phase-forming polymer (PFP); such as a surfactant, is mixed into the solution. When the temperature or other physical quantity exceeds or falls below a critical level (cloud point), said phase-forming polymer causes an initially homogeneous solution to separate into two macroscopic phases, the PFP (surfactant) being almost exclusively enriched in one of the phases.

The advantages of CP-ATPS over classic ATPS are, on the one hand, that it allows recovery of the substance used to form the ATPS. On the other hand, such systems allow the accurate separation of, for example, cell debris because, due to the very low interfacial tension between the phases, the tendency for solids to accumulate at the phase boundary is low. However, an interfacial tension which would be considered low even for ATPS and the small density difference between the phases to be separated lead to an even lower tendency for coalescence and a very slow and frequently incomplete phase separation.

SUMMARY

An aspect of the present invention is to provide a CP-ATPS method for magnetically assisted extraction which can also be used on an industrial scale and which allows efficient separation and purification of biomolecules even from solids-containing media and, in particular, improves the recyclability of the components of the system while increasing the selective separation efficiency in only one step.

In an embodiment, the present invention provides a method for magnetically assisted extraction of a target substance from an aqueous solution containing a plurality of components includes mixing a surfactant and functional magnetic particles having affinity for the target substance into the aqueous solution containing the target substance so as to bind the target substance to the functional magnetic particles and form a particle-containing single-phase aqueous surfactant solution. The particle-containing single-phase aqueous surfactant solution is transitioned to a two-phase state, a first particle- and surfactant-containing disperse phase being formed within a surrounding second phase, the absorption capacity of the first particle- and surfactant-containing disperse phase being lower for unbound dissolved functional magnetic particles than that of the surrounding second phase. The first particle- and surfactant-containing disperse phase and the surrounding second phase are separated using a magnetic field. The first particle- and surfactant-containing disperse phase is separated.

BRIEF DESCRIPTION OF THE DRAWINGS

The present invention is described in greater detail below on the basis of embodiments and of the drawings in which the term "surfactant" is always understood to include the alternative use of PFP. In the drawings.

DETAILED DESCRIPTION

Figure 1:
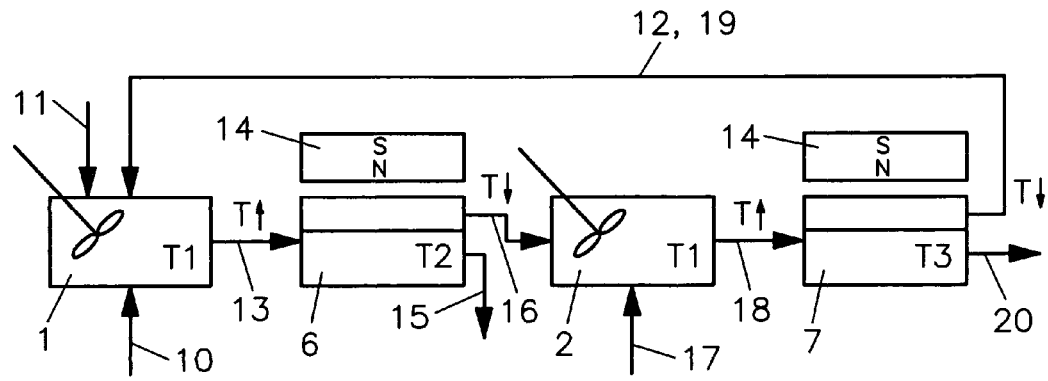
FIG. 1 is a basic block diagram of an example of an SMEP method.

In an embodiment, the present invention provides for a method for magnetically assisted extraction of a target substance from an aqueous solution containing several components. This method is referred to as SMEP method (SMEP=Smart Magnetic Extraction Phases). In this method, functional magnetic particles having an affinity for the desired target substance are mixed into the aqueous solution containing the target substance to be extracted (initial solution). In the process, the target substance binds, for example, chemically or adhesively, to said particles. In a subsequent step, a PFP, such as a surfactant, can be added to the aqueous solution containing the magnetic particles, the resulting solution having a cloud point (CP).

When the cloud point (CP) is crossed, the solution, or components thereof, undergoes a transition from a single-phase to a two-phase state, or vice versa, depending on the direction in which the crossing occurs. The cloud point is usually represented by a specific temperature, the cloud temperature. The single-phase state generally exists at temperatures below the cloud temperature, while the two-phase state (which, in the case of a thoroughly dispersed mixture, is turbid) exists at temperatures thereabove. The cloud point is influenced by the composition of the solution, such as by the concentration of the PFP or surfactant in the solution.

The cloud point in the present invention may also be determined by other quantities. Instead of or in combination with a temperature value, the cloud point may also be determined by a pH value, an ionic strength, or a combination of several quantities, the above-mentioned phase change being controllable by changing the pH value or the ionic strength.

The above-mentioned addition of the PFP or surfactant initially produces a single-phase aqueous surfactant solution (or PFP solution, hereinafter inclusively referred to as "surfactant solution"), which is then caused to undergo a transition to a two-phase state as described above, optionally after being subjected to additional homogenization steps. In the process, a first, surfactant-containing (i.e., PFP-containing) disperse phase is formed within a surrounding second phase, beginning at the particles having the target substance bound thereto. The absorption capacity of the surfactant-containing (PFP-containing) phase for all substances that are not bound to the particles, or at least for the substances to be separated from the target substance, is lower than that of the second phase. It is only the target substance to be separated that is bound by the functional magnetic particles and thus held in the surfactant-containing phase (PFP-containing phase) by said particles.

In a further step, the phases can be separated in the two-phase region under the action of a magnetic field. Magnetic forces act selectively on the magnetic particles, drawing them toward higher magnetic field strengths along with the target substance bound thereto and the surfactant- or PFP-containing phase. There, the coalesced surfactant-containing phase can then be separated from the second phase, for example, by suction, together with the magnetic particles and the target substance for further processing.

The use of a surfactant (or a PFP) having the above-mentioned properties (substantial exclusion of all relevant substances) is useful in combination with functional magnetic particles, but then has several advantages. Without the use of nanoparticles or microparticles that bind the target substance and transfer them into the disperse phase in the bound state, an ATPS in which all biomolecules are virtually excluded from one phase would be useless for bioseparation because no separation of materials takes place. Conversely, however, the use of the nanoparticles and microparticles together with an ATPS in which biomolecules are virtually excluded from the disperse phase is particularly advantageous only in combination with a CP-ATPS that can be reversibly switched between a single-phase state and a two-phase state by changing a parameter. However, in the case of a conventional ATPS, which is always in the two-phase state, the particles would permanently be surrounded by the polymer-rich phase from which the target substance is excluded.

It would therefore be impossible for the target substance to be bound to the particles, so that the desired separation of materials would also be impossible.

Figure 2:
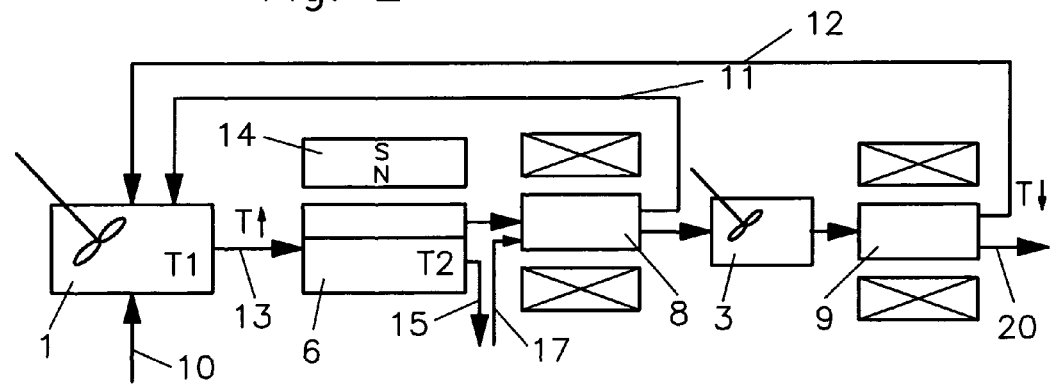
FIG. 2 is a block diagram of an example of an SMEP method in which the functional magnetic particles (FMP) and the surfactant are recirculated separately.
Figure 3:
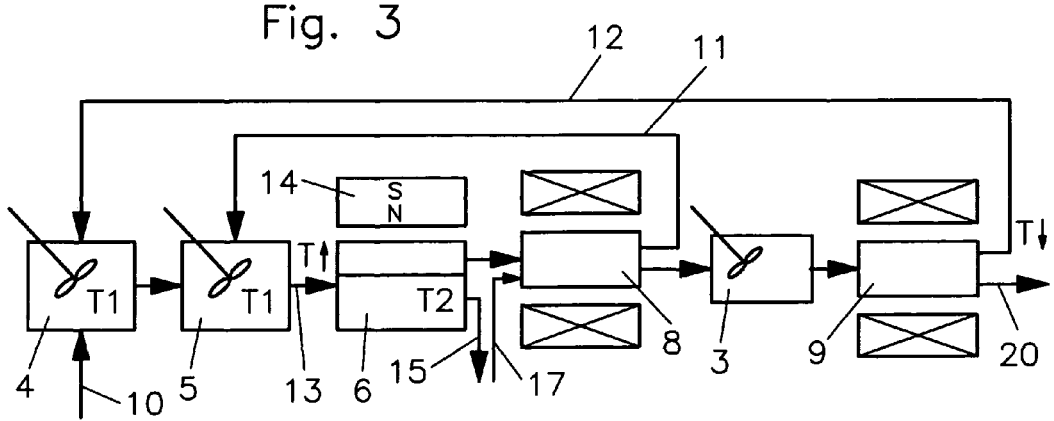
FIG. 3 is a block diagram of an SMEP method which is similar to that of FIG. 2 with the exception that the recirculated functional magnetic particles and surfactants are fed in at different points in time.

All examples of the method shown in FIGS. 1 through 3 have in common that they are carried out in a cascade of several mixing vessels 1 through 5 and magnetic separators 6 through 9, and that the initial medium 10 (aqueous solution) which, in addition to the desired target substance (for example, a biomolecule such as a protein), contains a plurality of undesired accompanying substances, is brought together with functional magnetic particles 12 and surfactant 11 to form a mixture solution 13, the solution being switched back and forth between a single-phase state and a multi-phase state by changing a parameter (in the examples only the temperature (T1 and T2)), and, upon phase separation, the separated phases being able to be removed as separate material streams. In the example, temperature T1 is lower than the cloud point (CP value), while temperature T2 is higher than the cloud point (CP value).

Functional magnetic particles 12 come into contact with the target substance in the solution, binding it selectively and with high affinity. The functional magnetic particles may be functionalized with any of the groups known in the processing of bioproducts, such as, for example, ion-exchange active molecules, hydrophobically interacting molecules, group-specific ligands, such as metal-chelate formers and protein A or specific antibodies.

FIG. 1 shows a basic block diagram of a "Smart Magnetic Extraction Process" (SMEP method). Initial aqueous solution 10 is introduced into a first mixing chamber 1 along with functional magnetic particles 12 and surfactant 11 and therein brought to a temperature T1, a single-phase aqueous surfactant solution being formed in the process. The functional magnetic particles have an affinity for the target substance to be separated and bind it to themselves.

In accordance with the present invention, functional magnetic particles 12 and surfactant 11 are mixed into the initial solution either simultaneously (in parallel) or one after the other (serially). However, introducing the magnetic particles first and subsequently adding the surfactant always leads to faster binding of the target substance to the magnetic particles because the surfactant, which displaces the target substance, and especially so if the surfactant itself attaches to the particles, cannot hinder the binding of the target substance to the particles as long as it is not added to the mixture.

The single-phase aqueous surfactant solution is subsequently removed from first mixing chamber 1 as a mixture solution 13 and heated to a temperature T2 above the cloud point, thereby causing it to undergo a transition to a two-phase state, and is introduced into first magnetic separator 6 while in this state.

In this example, the parameter used to bring the ATPS to the single-phase or two-phase state is temperature, but it would also be possible to use other operating parameters, such as the ionic strength or the pH value.

The functional magnetic particles loaded with the target substance are quantitatively transferred into the surfactant-rich (polymer-rich) disperse phase, as assumed. However, unbound biomolecules and solids, such as cell debris, remain in the homogeneous surfactant-depleted (or PFP-depleted) second phase. Due to the magnetic properties of the functional magnetic particles, the phase separation, which starts after the temperature is increased, can be significantly accelerated by a superimposed magnetic field (illustrated by a permanent magnet) acting on the magnetic particles in first magnetic separator 6, said magnetic field being provided by permanent magnets 14 or similarly acting magnetic field sources.

After the phase separation is completed, the phase containing the impurities is removed as a wastewater stream 15, and the surfactant-containing phase 16 containing the particles is cooled to a temperature T1 below the cloud point and fed into a second mixing chamber 2.

In second mixing chamber 2, a substance is mixed into the phase which is present as a single phase which substance, as an aqueous elution buffer 17, causes the bound target substance to separate from the functional magnet particles. At the end of this step, the target substance exits the second mixing chamber in an unbound, dissolved state in mixture 18. After that, mixture 18 is heated to a temperature T3 above the cloud point of the mixture and fed into a second magnetic separator 7 having permanent magnets 14.

Thus, the mixture introduced into second magnetic separator 7 is in a two-phase state, one phase containing the target substance and the other phase containing the magnetic particles. In the process, the functional magnetic particles are transferred into the polymer-rich disperse phase again. However, since the target substance is now in a free dissolved form, it is displaced from the polymer-rich phase and is completely enriched in the polymer-depleted phase. After a phase separation which, again, is accelerated by a superimposed magnetic field, the target molecule can be removed as a product via the polymer-poor phase. This product is present in a solids-free, purified form. The phase containing the functional magnetic particles 12 is fed into the first mixing chamber, thereby providing for particle recycling 19, while the phase containing the separated, isolated target substance solution 20 is removed for a further use (not shown).

The eluted functional magnetic particles and a substantial portion of the surfactant can always be recycled within the process. In the ideal case, the elution agent is also excluded from the polymer-rich phase, allowing direct recycling.

FIG. 2, in turn, shows an example of a method which is characterized firstly in that the functional magnetic particles (FMP) and the surfactant are recirculated separately into first mixing chamber 1, and secondly in that it makes use of high-gradient magnetic separators 8, 9 for separating functional magnetic particles 12 from a homogeneous phase.

In this process, first, surfactant 11 is separated from the particles in high-gradient magnetic separator 8 and recycled into first mixing chamber 1. The retained particles carrying the target substance are conveyed into mixing chamber 3. For example, the first high-gradient magnetic separator is operated cyclically; i.e., the separation of the surfactant is carried out in a first sub-step, while in a second sub-step, the particles retained in the high-gradient magnetic separator are washed out therefrom with an elution buffer 17.

The elution buffer containing the particles is then conveyed into third mixing chamber 3, where the actual separation of the target substance from the particles takes place. The separation of the magnetic particles is then carried out in a second high-gradient magnetic separator 9.

The recycled functional magnetic particles 12 and recycled surfactant 11 are both introduced into the first agitator vessel; i.e., they are mixed together into the aqueous solution containing the target substance (initial solution 10).

As in the exemplary method described above and shown in FIG. 1, mixing is carried out at a temperature T1 below the cloud point of the single-phase aqueous surfactant solution produced. Similarly, this solution is heated to a temperature T2 above the cloud point; i.e., it is introduced into a first magnetic separator 6 while in a two-phase state, and is separated therein into a wastewater stream 15 and the surfactant-containing second phase 16 under the action of a magnetic field (permanent magnet 14 or similarly acting magnetic field source).

In a departure from the first-mentioned exemplary experiment (see FIG. 1), the surfactant-containing second phase 16 is mixed with an aqueous elution buffer 17 only after the dissolved surfactants contained in said phase have been separated. The separation is carried out in a first high-gradient magnetic separator 8, for example, before the particle- and surfactant-containing phase is cooled again. The surfactants separated therein are recycled directly into the first mixing chamber, while the particles carrying the target substance are conveyed into mixing chamber 3 together with an elution buffer 17.

Finally, it is also conceivable that, in the single-phase region, the surfactants used may exert a negative effect on the binding of the target molecules to the functional magnetic particles. In this case, it is advantageous to modify the exemplary experiment of FIG. 2 in such a way that the separate recirculation and admixture of surfactants 11 (PFP) and functional magnetic particles 12 (FMP) is also used in the binding step (see FIG. 3). In this case, in a first step, initial solution 10 is initially mixed only with functional magnetic particles 12 in a fourth mixing chamber 4 to form an aqueous solution, so that the binding process can take place without being negatively affected by the surfactants. Subsequently, the aqueous solution is conveyed into a fifth mixing chamber 5 where surfactants 11 (or PFP) are then added. The remaining process sequence is the same as that illustrated in FIG. 2.

The present invention is not limited to embodiments described herein; reference should be had to the appended claims.

LIST OF REFERENCE NUMERALS

1 first mixing chamber
2 second mixing chamber
3 third mixing chamber
4 fourth mixing chamber
5 fifth mixing chamber
6 first separator
7 second separator
8 first high-gradient magnetic separator
9 second high-gradient magnetic separator
10 initial solution
11 surfactant
12 functional magnetic particles
13 aqueous surfactant solution
14 permanent magnet
15 wastewater stream
16 surfactant-containing phase
17 elution buffer
18 mixture
19 particle recycling
20 target substance solution

What is claimed is:

1. A method for magnetically assisted extraction of a target substance from an aqueous solution containing a plurality of components, the method comprising:
   mixing a surfactant and functional magnetic particles having affinity for the target substance into the aqueous solution containing the target substance so as to bind the target substance to the functional magnetic particles and form a particle-containing single-phase aqueous surfactant solution;
   transitioning the particle-containing single-phase aqueous surfactant solution to a two-phase state, a first particle- and surfactant-containing disperse phase being formed within a surrounding second phase, an absorption capacity of the first particle- and surfactant-containing disperse phase being lower for unbound dissolved functional magnetic particles than that of the surrounding second phase;
   separating the first particle- and surfactant-containing disperse phase and the surrounding second phase using a magnetic field; and
   separating the first particle- and surfactant-containing disperse phase.

2. The method recited in claim 1, further comprising:
   adding an aqueous elution buffer to the first particle- and surfactant-containing disperse phase so as to form a mixture;
   transitioning the mixture to a single-phase state solution so as to separate the target substance from the functional magnetic particles;
   transitioning the single-phase state solution to a two-phase state solution, a first phase containing the target substance and a second phase containing the magnetic particles; and
   separating the first phase containing the target substance and the second phase containing the magnetic particles using a magnetic field.

3. The method as recited in claim 2, wherein the functional magnetic particles and the surfactant are mixed in parallel into the aqueous solution containing the target substance.

4. The method as recited in claim 2, wherein first the functional magnetic particles and then the surfactant are mixed serially into the aqueous solution containing the target substance.

5. The method as recited in claim 1, further comprising magnetically separating the functional magnetic particles bound to the target substance from the first particle- and surfactant-containing disperse phase after the first particle- and surfactant-containing disperse phase is separated from the surrounding second phase.

6. The method as recited in claim 1, wherein the transitioning includes changing a temperature.

7. The method as recited in claim 1, wherein the transitioning includes changing a pH value of the solution.

8. The method as recited in claim 1, wherein the transitioning includes changing an ionic strength.

9. The method as recited in claim 2, wherein the transitioning of the mixture to a single-phase state solution includes changing a temperature.

10. The method as recited in claim 2, wherein the transitioning of the mixture to a single-phase state solution includes changing a pH value of the solution.

11. The method as recited in claim 2, wherein the transitioning of the mixture to a single-phase state solution includes changing an ionic strength.

12. The method as recited in claim 2, wherein the transitioning of the single-phase state solution to a two-phase solution includes changing a temperature.

13. The method as recited in claim 2, wherein the transitioning of the single-phase state solution to a two-phase solution includes changing a pH value of the solution.

14. The method as recited in claim 2, wherein the transitioning of the single-phase state solution to a two-phase solution includes changing an ionic strength.

* * * * *